(12) United States Patent
Carmi (10) Patent No.: US 12,141,979 B2
(45) Date of Patent: Nov. 12, 2024

(54) IMAGE DATA PROCESSING TO INCREASE FOLLOW-UP ANALYSIS FIDELITY

(71) Applicant: GE Precision Healthcare LLC, Waukesha, WI (US)

(72) Inventor: Raz Carmi, Haifa (IL)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/458,416

(22) Filed: Aug. 30, 2023

(65) Prior Publication Data
US 2023/0410313 A1 Dec. 21, 2023

Related U.S. Application Data

(62) Division of application No. 17/001,342, filed on Aug. 24, 2020, now Pat. No. 11,776,125.

(51) Int. Cl.
| | |
|---|---|
| G06V 10/70 | (2022.01) |
| G06F 18/214 | (2023.01) |
| G06N 3/045 | (2023.01) |
| G06T 7/00 | (2017.01) |
| G16H 30/20 | (2018.01) |

(52) U.S. Cl.
CPC ........ *G06T 7/0016* (2013.01); *G06F 18/2148* (2023.01); *G06N 3/045* (2023.01); *G06V 10/70* (2022.01); *G16H 30/20* (2018.01)

(58) Field of Classification Search
None
See application file for complete search history.

(56) References Cited

U.S. PATENT DOCUMENTS

| | | | | |
|---|---|---|---|---|
| 11,755,888 | B1* | 9/2023 | Zhang ................ | G06N 3/0475 706/15 |
| 2017/0236294 | A1* | 8/2017 | Fisher ................ | A61B 5/0042 600/419 |
| 2019/0087687 | A1* | 3/2019 | Danielsson ........... | G06F 16/56 |
| 2020/0311490 | A1* | 10/2020 | Lee .................... | G06T 5/60 |
| 2020/0394458 | A1* | 12/2020 | Yu ..................... | G06V 10/82 |
| 2021/0007695 | A1* | 1/2021 | Lu ..................... | G06T 11/003 |
| 2021/0092459 | A1* | 3/2021 | Cheong ............... | H04N 19/137 |
| 2022/0058804 | A1* | 2/2022 | Carmi ................ | G06F 18/2148 |

\* cited by examiner

*Primary Examiner* — Tsung Yin Tsai (57) ABSTRACT

Techniques are provided for improving image data quality, such as in functional imaging follow-up studies, using reconstruction, post-processing, and/or deep-learning enhancement approaches in a way that automatically improves analysis fidelity, such as lesion tracking fidelity. The disclosed approaches may be useful in improving the performance of automatic analysis methods as well as in facilitating reviews performed by clinician.

4 Claims, 9 Drawing Sheets

IMAGE DATA PROCESSING TO INCREASE FOLLOW-UP ANALYSIS FIDELITY

CROSS-REFERENCE TO RELATED APPLICATIONS

This application is a divisional of U.S. application Ser. No. 17/001,342, filed on Aug. 24, 2020, the disclosure of which is incorporated herein by reference in its entirety.

BACKGROUND

The subject matter disclosed herein relates to analysis of longitudinal (i.e., follow-up) images acquired using medical imaging systems, such as functional imaging systems.

Diagnostic imaging technologies allow images of internal features of a patient to be non-invasively obtained and may provide information about the function and integrity of the patient's internal structures. Diagnostic imaging systems may operate based on various physical principles, including the emission or transmission of radiation from the patient tissues. For example, single photon emission computed tomography (SPECT) and positron emission tomography (PET) may utilize a radiopharmaceutical that is administered to a patient and whose breakdown results in the emission of gamma rays from locations within the patient's body. The radiopharmaceutical is typically selected so as to be preferentially or differentially distributed in the body based on the physiological or biochemical processes in the body. For example, a radiopharmaceutical may be selected that is preferentially processed or taken up by tumor tissue. In such an example, the radiopharmaceutical will typically be disposed in greater concentrations around tumor tissue within the patient.

In the context of PET imaging, the radiopharmaceutical typically breaks down or decays within the patient, releasing a positron which annihilates when encountering an electron and produces a pair of gamma rays moving in opposite directions. In SPECT imaging, a single gamma ray is generated when the radiopharmaceutical breaks down or decays within the patient. These gamma rays interact with detection mechanisms within the respective PET or SPECT scanner, which allow the decay events to be localized, thereby providing a view of where the radiopharmaceutical is distributed throughout the patient. In this manner, a caregiver can visualize where in the patient the radiopharmaceutical is disproportionately distributed and may thereby identify where physiological structures and/or biochemical processes of diagnostic significance are located within the patient.

In functional medical imaging contexts, such as those employing PET and SPECT scanners, it is common to perform follow-up studies involving at least two scans of the same patient acquired at different times, such as over the course of a treatment or therapy regime. Such procedures can be used to monitor or evaluate the physiological response to a medical treatment and can help planning further patient care. In the analysis of follow-up scans, a reviewer may compare the image values on relevant tissue regions or organs and assesses the radiotracer activity differences. For example, if an identified lesion shows significantly reduced tracer uptake after a therapy course, this may indicate good response to the therapy procedure. Otherwise, if the lesion shows increasing tracer uptake, this may indicate no response and disease progression (i.e. medical condition deterioration).

In practice, functional imaging follow-up studies are performed with various radiotracers and for a variety of different diseases, often using different protocols. The characteristics of the images acquired may therefore differ widely between studies, and even between successive scans of the same patient, which may be acquired months apart and/or using different scanners. These differences in image characteristics may be problematic in assessing follow-up images of a patient. For example, lesion tracking with comparative quantitative analysis can depend largely on the overall image quality, small feature sharpness, image noise, and enhancement of specific learned structures over others. Automatic analysis algorithms may be even more sensitive to such variations than a skilled human.

BRIEF DESCRIPTION

In one embodiment, an image processing system is provided. In accordance with this embodiment, the image processing system comprises: one or more memory structures storing processor-executable code and one or more processors in communication with the one or more memory structures. The processor-executable code, when executed by the one or more processors, cause the one or more processors to perform acts comprising: receiving a set of corresponding image sub-volumes, wherein each image sub-volume of the set comprises a corresponding region of interest; calculating a similarity metric and a sharpness metric using the set of image sub-volumes; determining a fidelity metric based on the similarity metric and the sharpness metric; varying one or more parameters of an image processing or image generation routine or routines; determining a calculated fidelity metric for each variation of the image processing routine or routines as applied to the set of image sub-volumes; and selecting a respective image processing routine based upon the calculated fidelity metrics.

In a further embodiment, an image processing system is provided. In accordance with this embodiment, the image processing system comprises: one or more memory structures storing processor-executable code and one or more processors in communication with the one or more memory structures. The processor-executable code, when executed by the one or more processors, cause the one or more processors to perform acts comprising training a deep learning network model for image enhancement. Training the deep learning network model is performed by iteratively performing steps comprising: receiving a first input image volume and a second input image volume; providing the first input image volume and the second input image volume to the deep learning network model, wherein the deep learning network model is configured to respectively output a first output image volume and a second output image volume; comparing the first output image volume and the second output image volume based on a fidelity metric comprising a measure of structural similarity, wherein a loss function for the deep learning network model is based on the fidelity metric and training the deep learning network model is based on reduction or minimization of the loss function.

In an additional embodiment, a processor-implemented method for enhancing images is provided. In accordance with the embodiment, steps are performed that comprise: acquiring an image volume as part of a follow-up study of a patient; processing the image volume to generate an enhanced image volume using a deep learning network model trained to generate the enhanced image volume or using an image processing routine selected or parameterized based on a calculated fidelity metric; and providing the enhanced image volume for review as part of the follow-up study.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

In functional medical imaging contexts, such as may be performed using PET or SPECT imaging, follow-up studies may be performed to assess patient response to a treatment or therapy and/or to otherwise evaluate a physiological characteristic of a patient over time. Such follow-up studies, which may also be described as longitudinal studies, typically involve at least two scans of the same patient acquired at different times.

The characteristics of the images acquired may differ widely even between successive scans of the same patient, which may be acquired months apart and/or using different scanners. These differences in image characteristics may be problematic in assessing follow-up images of a patient. For example, lesion tracking with comparative quantitative analysis can depend largely on the overall image quality, small feature sharpness, image noise, and enhancement of specific learned structures over others. Automatic analysis algorithms may be even more sensitive to such variations than a skilled human. The present techniques help address these issues and to provide improved functional imaging follow-up analysis, especially where it is based on automatic tools and analysis algorithms.

With the preceding in mind, image analysis for lesion tracking comparison is focused, in general, on the mutual assessment of selected candidate lesions or other pathologies. This is somewhat different than single study assessment where there is no comparative reference to evaluate the potential clinical findings. Typically, a reviewer, who may be assisted by a dedicated automatic algorithm and/or software tool(s), selects pairs of lesions (one in each respective scan of a pair of scans), each acquired at a different time. The overall diagnostic process generally comprises an a priori assumption that there is, at least in average, some correspondence between a selected pair of structures and their values. As discussed herein, this presumed, mutual correspondence can be used to optimize the input images prior to assessment to provide better fidelity for the relevant diagnostic purpose.

By way of example, as discussed herein techniques are provided for improving (e.g., optimizing) image data quality in functional imaging follow-up studies using reconstruction, post-processing, and/or deep-learning enhancement approaches in a way that automatically improves (e.g., maximizes) relevant lesion-tracking analysis fidelity. Though PET and SPECT imaging examples are used herein in order to provide a useful real-world context and suitable examples, it should be appreciated that the present techniques may be implemented with other suitable functional imaging modalities including, but not limited to functional magnetic resonance (MR) imaging and functional computed tomography (CT) imaging. The parameters of a selected image enhancement method are trained or varied iteratively to improve (e.g., maximize or optimize) a pre-determined fidelity metric applied on lesion sub-volume pairs. In certain embodiments, the training or iterative improvement utilizes multiple selections of lesion or structure pairs in successive patient scans (while assuming statistically significant correspondence or correlation between follow-up lesions). In some implementations, synthetic structure data may be employed in addition to or in place of the patient scan data. The lesion correspondence postulation, which is relevant to follow-up studies, can significantly reduce noise and small false positive findings while increasing lesion contrast. The approach may be particularly useful in improving the performance of automatic analysis methods.

Figure 1:
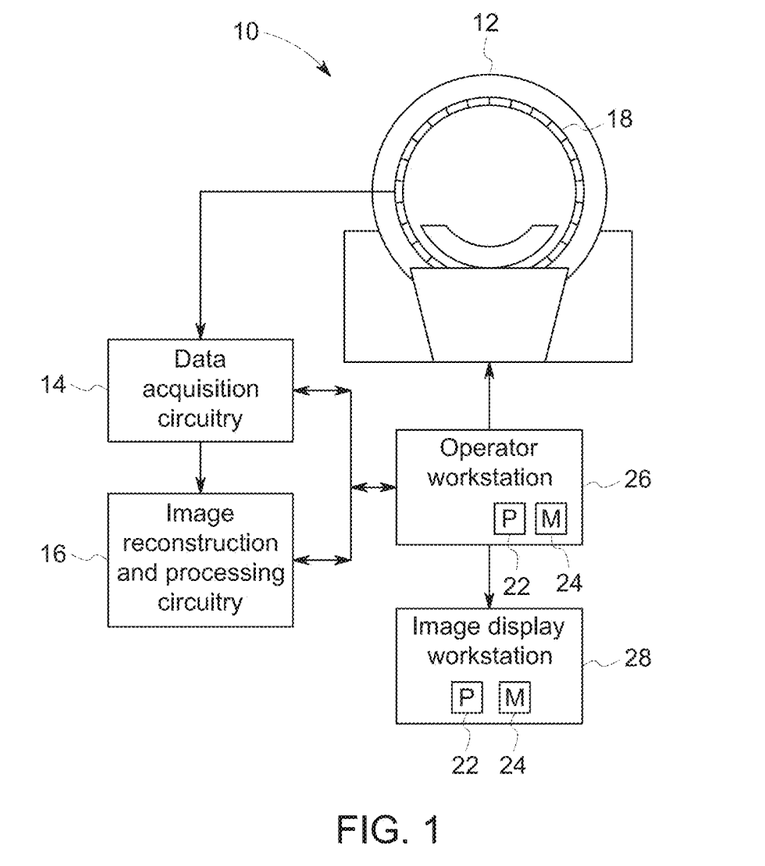
FIG. 1 is a diagrammatical representation of a nuclear medicine imaging system in accordance with aspects of the present disclosure.

With the preceding in mind and turning now to the drawings, FIG. 1 depicts a nuclear imaging system 10 (e.g., a positron emission tomography (PET) or a single photon emission computed tomography (SPECT) imaging system) operating in accordance with certain aspects of the present disclosure. Such a nuclear imaging system 10 may be useful for what may be characterized as functional or physiological imaging, in which the acquired image data may be used to visualize or otherwise detect characteristics of, or changes in, metabolism, blood flow, localized chemical composition, absorption or differential absorption of biomarkers, and so forth. Such a functional imaging modality may be used in isolation or in conjunction with another imaging modality, such as a CT imaging system, which may be useful for what may be characterized as structural imaging where anatomic structure is characterized or visualized. Though PET and SPECT imaging systems are primarily discussed herein, it should be appreciated that the present techniques may also be useful in other functional imaging contexts, such as in a functional magnetic resonance (MR) imaging system, a functional CT imaging system, certain ultrasound imaging approaches, and so forth.

Returning now to FIG. 1, the depicted nuclear imaging system 10 (here depicted as a PET imaging system for the purpose of illustration) includes a detector assembly 12, data acquisition circuitry 14, and image reconstruction and processing circuitry 16. The detector assembly 12 of a nuclear imaging system 10 (e.g., a PET or SPECT imaging system) typically includes a number of detector modules (generally designated by reference numeral 18) arranged in one or more rings or partial rings, as depicted in FIG. 1. In practice, the detector modules 18 are used to detect radioactive emissions from the breakdown and annihilation of a radioactive tracer administered to the patient. By determining the paths traveled by such emissions, the concentration of the radioactive tracer in different parts of the body may be estimated. By way of example, in a PET or SPECT context the detector assembly 12, via the modules 18, may be configured to generate signals in response to gamma rays generated by positron annihilation events and emitted from a subject within the imaged volume. In certain implementations, the detector assembly 12 can include scintillators and photon detection electronics. The detector assembly 12 may be of any suitable construction and configuration for acquiring PET or SPECT data. In the context of a SPECT imaging system, the nuclear imaging system 10 will typically also include a collimator assembly associated with the detector assembly 12 to allow line-of-flight information to be determined for detection events.

In certain such implementations, gamma rays may be converted, such as in a scintillator of the detector assembly 12 or detector modules 18, to lower energy photons (e.g., optical photons) that in turn may be detected and converted in the detector modules 18 to electrical signals, which can be conditioned and processed to output digital signals. In a PET imaging context, these output signals can be used to match pairs of gamma ray detections as corresponding to the same annihilation event, allowing a linear path to be determined for the pair. That is, in such a PET implementation, when two gamma rays strike opposing detectors in temporal coincidence it may be determined that a positron annihilation occurred somewhere on the line connecting the two impact locations (absent the effects of interactions of randoms and scatter detections). In a SPECT imaging context, line of flight information is instead inferred based at least in part on the collimation associated with the detector assembly, which limits detected events to a narrow angular range. The collected data can be sorted and integrated and used in subsequent processing such as by image reconstruction and processing circuitry 16.

Thus, in operation, the detector acquisition circuitry 14 is used to read out the signals from the detector modules 18 of the detector assembly 12, where the signals are generated in response to gamma rays emitted within the imaged volume. The signals acquired by the data acquisition circuitry 14 are provided to the image reconstruction and processing circuitry 16. The image reconstruction and processing circuitry 16 generates an image based on the derived gamma ray emission locations. The operator workstation 26 is utilized by a system operator to provide control instructions to some or all of the described components and to configure the various operating parameters that aid in data acquisition and image generation. The operating workstation 26 may also display the generated image. Alternatively, the generated image may be displayed at a remote viewing workstation, such as the image display workstation 28. In practice, the respective images may be stored as part of an electronic record for a patient, such as in an image archiving system, accessible by various computers and/or image viewing workstations, such that images acquired of a patient at different times and locations may be viewed and compared, such as to facilitate evaluation of a patient condition over time (e.g., over the course of a treatment regime).

It should be appreciated that, to facilitate explanation and discussion of the operation of the nuclear imaging system 10, the data acquisition circuitry 14 and the image reconstruction and processing circuitry 16 have been shown separately in FIG. 1 from other illustrated components (e.g., the detector assembly 12, the operator workstation 26, and the image display workstation 28). However, it should be appreciated that, in certain implementations, some or all of these circuitries may be provided as part of the detector assembly 12, the operator workstation 26, and/or the image display workstation 28. That is, components shown as functionally separate in FIG. 1 may in practice be housed together or otherwise combined as part of a single device or shared circuitry. For example, the hardware, software, and/or firmware executed on or provided as part of the data acquisition circuitry 14, whether provided as part of the detector assembly 12, the operator workstation 26, and/or the image display workstation 28, may be used to perform various detector readout and/or control actions described herein. In certain implementations the data acquisition circuitry 14 may include specially configured or programmed hardware, memory 24, and/or special purpose processors 22 (e.g., application-specific integrated circuits (ASICs)). Similarly, certain of these image processing functions may be performed using one or more general or special purpose processors 22, whether part of the nuclear imaging system 10 or elsewhere, and stored code or algorithms configured to execute on such processors. Likewise, a combination of special purpose hardware and/or circuitry may be used in conjunction with one or more processors configured to execute stored code to implement the techniques discussed herein.

With the preceding system discussion in mind, and as noted herein, the presently disclosed techniques may be useful in the context of lesion follow-up analysis, in which clinical conclusions can depend on the accuracy in identifying corresponding relevant lesions in successive scans and the analysis accuracy of how the identified lesions develop or change over time. The change of the lesion over time may be assessed based on measured lesion characteristics in successive images, such as maximum and mean image intensity, lesion size (segmented volume), morphological structures, and lesion texture. Such feature measurements, and correct lesion identification, can be adversely affected by both image noise and artifacts, and by a too low image spatial resolution and feature contrast.

For example, PET-CT procedures may provide non-optimal image quality or accuracy for a variety of reasons, including, but not limited to: the use of reduced time-scans (e.g., to increase system capacity), reduced radiotracer dose, and/or the use of non-time of flight PET systems or other low-cost systems. In addition, some tracers may be associated with lower image quality than typical FDG scans, such as $^{68}$Ga-PSMA and $^{68}$Ga-DOTATATE and others, which is also related to the amount of physiological uptake in specific relevant targets. The resulting image problems and/or discrepancies can impact implementations of automatic detection and/or assessment routines, which may be more prone to data inaccuracies than a human expert. By way of example, assuming that in two successive follow-up scans a specific lesion does not change in its physiological and structural characteristics. However, the imaging appearance may be substantially different due to noise, artifacts, automatic mis-identification, etc. A corresponding mathematical follow-up analysis applied directly on these images may give dissimilar characteristics to the lesion and its appearance on the follow-up scan, despite the lesion being unchanged. With this in mind, the techniques described herein may be used to generated improved or enhanced images having similar lesion characteristics between scans, which may then be processed using the lesion analysis tools. That is, the disclosed techniques can capture and enhance the most relevant feature(s) of potential lesion structures that are useful for accurate medical diagnosis and can suppress non-relevant image feature(s) that can lead to inaccurate medical diagnosis. Such image enhancement may be useful in general to improve an image for analysis and may be of notable use in follow-up studies where two or more images are to be compared.

In particular, the presently disclosed approaches may be used to process imaging data acquired using a functional imaging system, such as the nuclear imaging system 10 described with respect to FIG. 1, to be suitable for use in patient follow-up studies or, more generally, to be improved for review and diagnostic purposes. By way of example, such approaches may be used to optimize image data quality in PET and SPECT functional imaging follow-up studies using either reconstruction, post-processing, or deep-learning enhancement techniques. In this manner, relevant lesion-tracking analysis fidelity may be improved (e.g., maximized).

In accordance with these approaches, multiple selections of lesion or structure pairs in successive patient scans may be generated or otherwise acquired. In certain applications, as discussed herein, synthetic structure data may be used in addition to or instead of acquired image data. Statistically significant correspondence or correlation between features (e.g., lesions) in follow-up scans is assumed and can be utilized (statistically) to reduce uncorrelated noise and false positive findings. The parameters of a selected image enhancement method are trained or varied iteratively to improve (e.g., maximize) a selected or otherwise pre-determined fidelity metric applied on lesion sub-volume pairs. The lesion correspondence postulation, which is relevant to follow-up studies, may be incorporated into processing of the images to reduce noise and false positive findings while increasing lesion contrast. In this manner, automatic analysis methods can be improved by improving the quality and/or comparability of the images subjected to analysis. That is, follow-up analysis comparisons can achieve higher accuracy since the image enhancement routines can be more effective and accurate. As discussed herein, both analytical (e.g., non-machine-learning) routines and/or deep-learning approaches may be employed in implementing these techniques.

Figure 2:
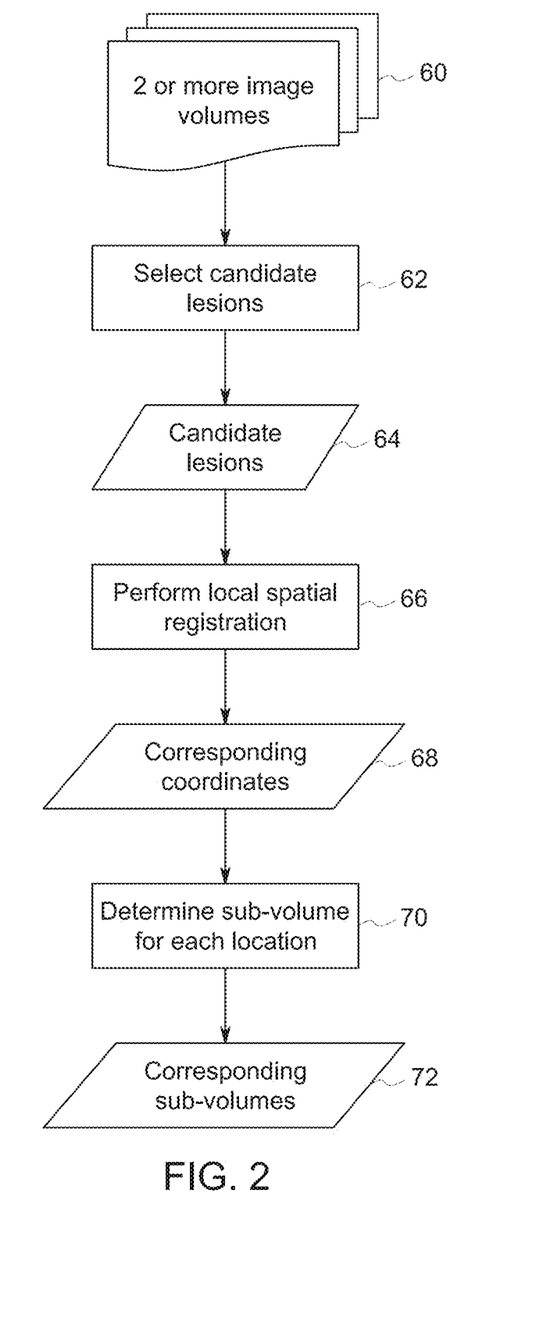
FIG. 2 depicts a process flow of steps employed to identify corresponding sub-volumes in an example of an analytical approach, in accordance with aspects of the present disclosure.
Figure 3:
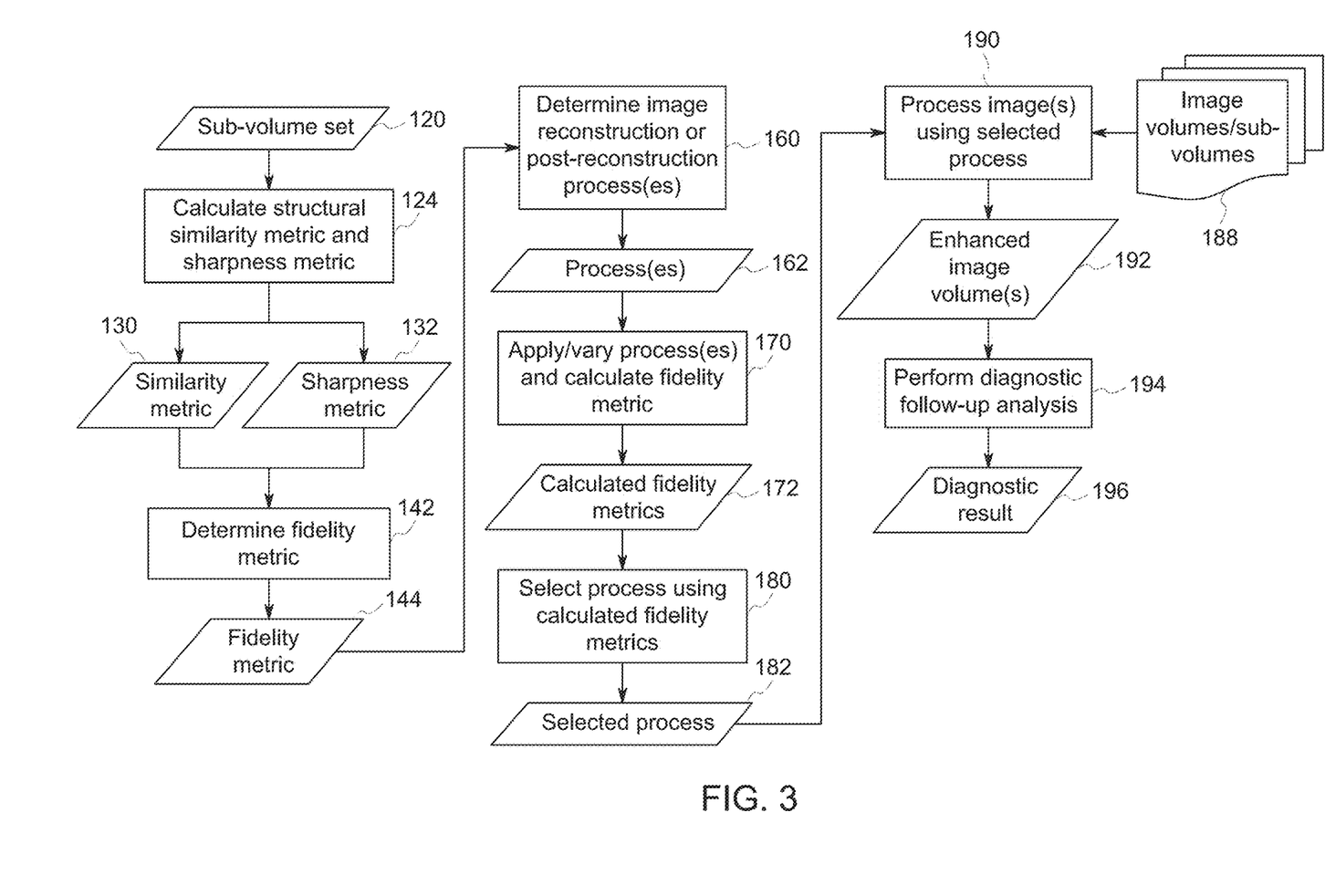
FIG. 3 depicts a process flow of steps employed to process a set of sub-volumes (e.g., a pair of sub-volumes) in an example of an analytical approach, in accordance with aspects of the present disclosure.

With the preceding in mind, the present disclosure relates examples of both an analytic implementation and a deep-learning based implementation, such as may be implemented in a machine learning context. Turning to FIGS. 2 and 3, an example of an automatic or semi-automatic tool that employs analytical (i.e. non-machine learning) image enhancement and analysis techniques is described first. In this example, a set of input image data 60 acquired using a functional imaging modality is provided. In one implementation, the input image data 60 includes at least two follow-up image volumes, such as successive scans of the same patient taken at different times with identical or comparable imaging protocols. If more than two successive scans are provided in the input image data, each scan can be evaluated either relative to the previous scan or relative to a first baseline scan.

A user, or an automatic algorithm, selects (step 62) candidate lesions 64 or structures for follow-up comparison on any of the two volumes of the input image data 60. The candidate lesions 64 (or other features) may serve as example structures for image enhancement as discussed herein. Selection at step 62 may be done via a dedicated interactive tool (e.g. by a mouse click), by other suitable selection interactions, and/or by an automated routine configured to identify lesions or other suitable features. The selection (step 62) of a set of lesions 64 or other features may be done in part on a first image volume, and in additional part on a second image volume. That is lesions or other features may be selected separately and independently on each image volume to be compared.

In practice, each candidate lesion 64 may be associated with a coordinate (e.g., an x, y, z Cartesian coordinate) within its respective image volume. For each selected lesion coordinate in the respective image volume and its surrounding voxels, a local spatial registration routine (step 66) finds a corresponding (i.e., paired) coordinate in the comparison image volume. Overall, a set of corresponding coordinate pairs (i.e., corresponding or paired coordinates 68) is determined (i.e., a coordinate in each image volume undergoing comparison). An example of one such local registration approach is discussed in greater detail below with respect to FIG. 4.

Based on the local registration results, a sub-volume 72 with a determined optimal size is determined (step 70) around each corresponding coordinate 68 (e.g. a location of a lesion in a first image volume and the corresponding follow-up lesion in the second image volume). Typically, the user (or an automatic algorithm) can select several example lesion-pairs in the patient body. In such an example, the process may be performed for some or all of the lesion pairs.

Turning to FIG. 3, for the purpose of evaluating a pair (or more) of corresponding sub-volume regions 72 (here depicted as a sub-volume set 120), a metric 130 for structural similarity and a metric 132 for lesion contrast or sharpness is calculated (step 124). A lesion-tracking fidelity metric 144 is determined (step 142) based on the lesion similarity metric 130 and sharpness (i.e., contrast) metric 132. In this manner a transformation function may be identified that can be applied on a given sub-volume pair 120 to generate new sub-volumes in a way that the structural similarity is improved while keeping sufficient (or improved) lesion sharpness or contrast. The target transformation function may also comprise inherent constraints which can prevent exaggerated image modification.

By way of further explanation, mathematical examples of useful fidelity metrics are provided. In one example, for a pair of sub-volumes A and B, a "mutual information" (MI) function (corresponding to a similarity metric 130 as used herein) is first calculated. This metric reflects or quantifies the level of correspondence between the sub-volume structures and may be given as:

$$MI = H(A) + H(B) - H(A,B) \quad (1)$$

where:

$$H(A,B) = -\text{SUM}_{a,b}[P_{AB}(a,b) \cdot \log(P_{AB}(a,b))] \quad (2)$$

$$H(X) = -\text{SUM}_X[P_X(X) \cdot \log(P_X(X))] \quad (3)$$

and P is calculated as a histogram (self or joint) and H is the entropy function. While the preceding relates one approach to generating a similarity metric 130, in other implementations the similarity metric 130 may be a correlation function or other measure of statistical similarity instead of a mutual information function.

With respect to the sharpness or contrast metric 132, in one implementation the standard deviation (STD) of each sub-volume (A and B) may be calculated to statistically reflect the "sharpness" of the lesion or structure. That is, the sharpness metrics 132 may be STD(A) and STD(B) in such an implementation. In one embodiment, the final fidelity metric (FM) 144 may be defined as:

$$FM = STD(A) \cdot STD(B) \cdot MI \quad (4)$$

As noted above, the fidelity metric 144 may also incorporate components that limit the extent to which the new images differ relative to the original images. For example, the fidelity metric 144 can include a mean squared error (MSE) like comparison between each new generated image and the original image. In such an approach, the standard MSE may also be clipped on a positive constant so that small variations will not be further minimized. In one such implementation, the fidelity metric 144, which may be maximized in this approach, as discussed below, may be defined as:

$$FM = (1 - MSE_C(A - A_0)) \cdot (1 - MSE_C(B - B_0)) \cdot STD(A) \cdot STD(B) \cdot MI \quad (5)$$

where $MSE_C$ is a clipped MSE (e.g., [zero-clipped] (MSE−constant)).

Once a suitable fidelity metric 144 has been determined for the sub-volume pair 120, the fidelity metric 144 may be used to identify a transformation function or image generation process (e.g., an optimal transformation function or image generation process) to be used in processing acquired image volumes. As shown in FIG. 3, one step that may be performed, at least in some implementations, is to determine (step 160) or otherwise identify a set of candidate processes 162 to be tested using the identified fidelity metric 144. Such candidate processes 162 may include, but are not limited to, image reconstruction processes or algorithms, post-reconstruction processes or algorithms, transformation functions, and so forth. Typically, such processes 162 may each include one or more parameters (e.g., hyperparameters) or values that can be varied (e.g., tuned) to affect implementation of the respective process. With this in mind, for the process or processes 162 under evaluation, each respective process may be varied or re-parameterized over a suitable operational range, the set of image sub-volumes 120 processed, and corresponding fidelity metrics calculated (step 170, whereby calculated fidelity metric 172 is generated) for the one or more varied processes 162. By way of example, a respective process 162 may be applied to the group 120 of lesion pair sub-volumes. For each variation or reparameterization of a respective process 162, the fidelity metric is calculated (step 180). In the circumstance of multiple lesion pairs being present in the sub-volumes in question, the calculated fidelity metrics 172 may be averaged across some or all of the lesion pairs to facilitate comparison and/or optimization. The fidelity metric calculation (step 180) is performed for each of the different image generation processes 162 or parameters. In another option, a suitable (e.g., optimal) parameter configuration can be found efficiently using 'stochastic gradient descent' techniques.

The respective calculated fidelity metric 172 for each varied or re-parameterized process 162 being evaluated may be used to select and/or parameterize (step 180) a process 182 (or process having suitable parameters) from among the candidate processes 162. For example, in one embodiment, a maximal or optimal fidelity may be determined (step 180) from the calculated fidelity metrics 172 where the maximal or optimal fidelity metric was calculated for a respective parameterized process 162 (e.g., image generation process or parameters for such a process) which becomes the selected process 182.

The selected process 182 can then be applied (step 190) to any suitable sub-volume pairs (e.g., lesion sub-volume pairs) or on the total patient image volume (depicted as Image Volumes/Sub-Volumes 188) to generate processed image volumes (i.e., enhanced image(s) 192) having improved (e.g., maximized or optimized) fidelity. A diagnostic analysis (e.g., a standard clinical diagnostic follow-up analysis) can then be performed (step 194) using the enhanced image volumes 192 to obtain a diagnostic result 196.

As noted above, and turning to FIG. 4, an example of one local registration (step 66) approach suitable for use with the preceding techniques is discussed in greater detail. In this example of a registration, a reference volume 220 and a secondary volume 222 serve as inputs. In practice, the reference volume 220 and the secondary volume 222 may be an initial image volume and a follow-up image volume taken of a patient at a later date. It should be understood that, in accordance with the registration process and present discussion, the reference volume 220 may be either the earlier or the later acquired image volume. In this example, the reference volume 220 and the secondary volume 222 may be reconstructed image volumes present in the set of input image data 60 of FIG. 2.

Figure 4:
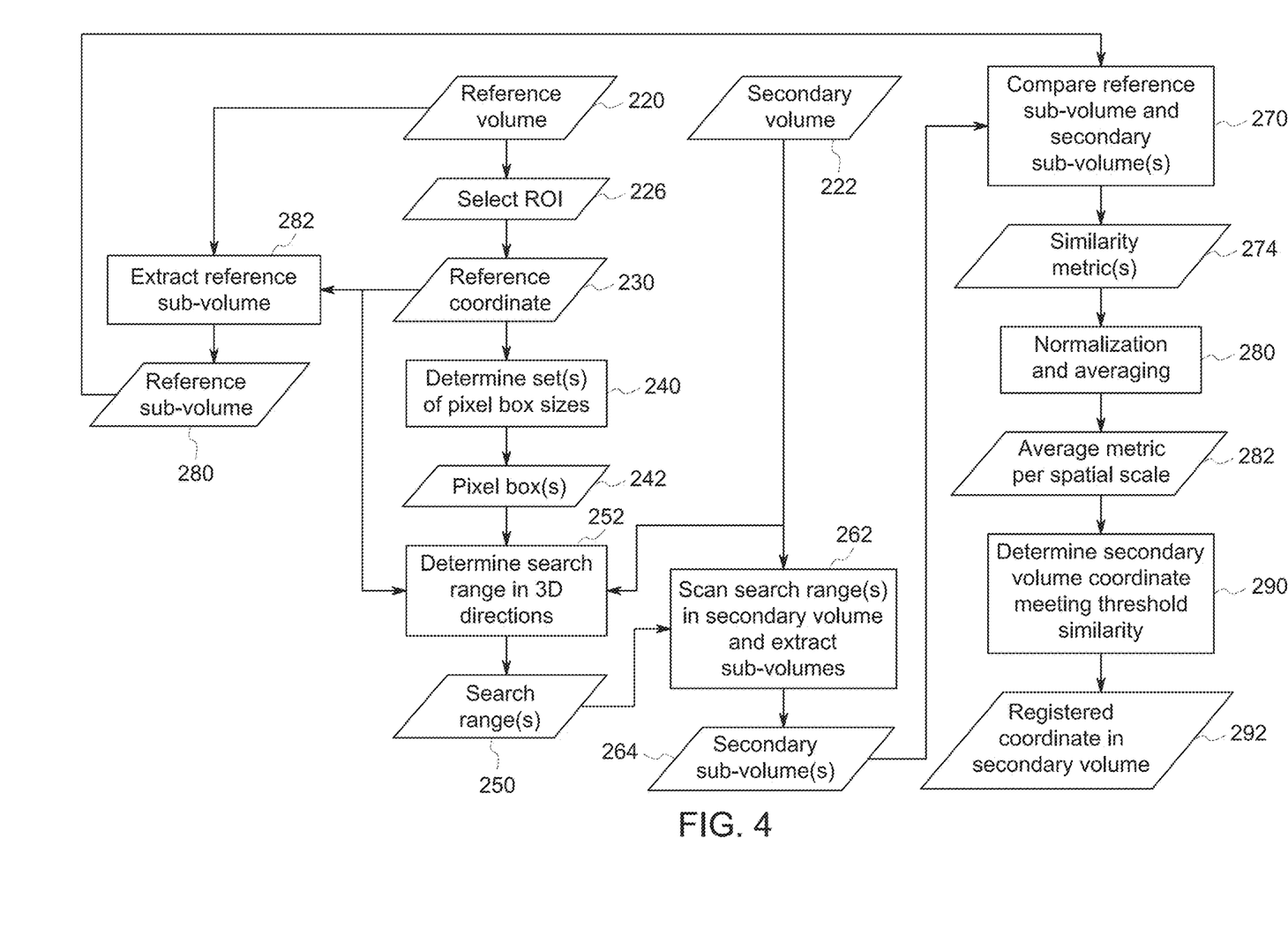
FIG. 4 depicts a process flow of steps employed to perform a local registration to identify coordinate pairs, in accordance with aspects of the present disclosure.

In one of the two volumes undergoing registration, here denoted the reference volume 220, a region of interest (e.g., a lesion or abnormality) is selected (step 226) either by a reviewer using a human interactive tool (e.g., mouse, touch screen, keyboard input, and so forth) while reviewing the displayed reference volume 220 or by an automated detection routine. A reference coordinate 230 within the reference volume 220 is calculated or otherwise determined based upon the selection at step 226, such as based upon a pixel or voxel selected by the reviewer, a center of mass or geometric center of the selected region (e.g., lesion), or other suitable techniques for establishing a representative coordinate for a selected region.

Based upon the determined reference coordinate 230 a set or sets of pixel box sizes 242 are determined (step 240) and used to identify or select neighbor voxels. In practice, the set of pixel box sizes 242 may be based on typical or representative structures (e.g., small typical lesions as measured in millimeters (mm)) and on a statistical estimation of the current selected structure size. By way of example, three box sizes may be determined at step 240 with side lengths of 15, 21, and 27 image pixels, respectively.

A search range or ranges 250 in three-dimensional (3D) directions is determined (step 252) for the secondary image volume 222. The search range(s) is centered around the reference coordinate 230. By way of example, a search range may be 47 pixels (or any other suitable range of pixels) in each dimension relative to the reference coordinate 230.

For each pixel box size 242, the registration process scans (step 262) the secondary volume 222 across the determined search ranges 250 and extracts sub-volumes 264. The extracted secondary sub-volumes 264 are compared (step 270) with a sub-volume 280 extracted (step 282) from the reference volume 220 based on the selected region of interest. The comparison at step 270 may be based on a statistical similarity metric 274. By way of example, in one implementation the comparison at step 270 for each two sub-volumes may be based on $$\text{Similarity} = \frac{1}{([\text{Sum of the Squared Difference}] + 1])} \quad (6)$$

In one implementation, volumetric comparison results (based on similarity metrics 274) are calculated for each pixel box size 242. The results with respect to each pixel box size in such an implementation may be normalized and averaged (step 280) in order to obtain an average metric 282 for each different spatial scale. A determination (step 290) may then be made as to which coordinate in the secondary volume 272 best meets or exceeds a threshold similarity to the reference coordinate 230. By way of example, the coordinate in the secondary volume 222 with the maximum determined similarity may be deemed the registered coordinate 292 (i.e., point) to the reference coordinate 230 in the reference volume 220. In such an example, the reference coordinate 230 and registered coordinate 292 may be corresponding coordinates 68, as referenced in FIG. 2, as a result of a local spatial registration being performed at step 66.

Figure 5:
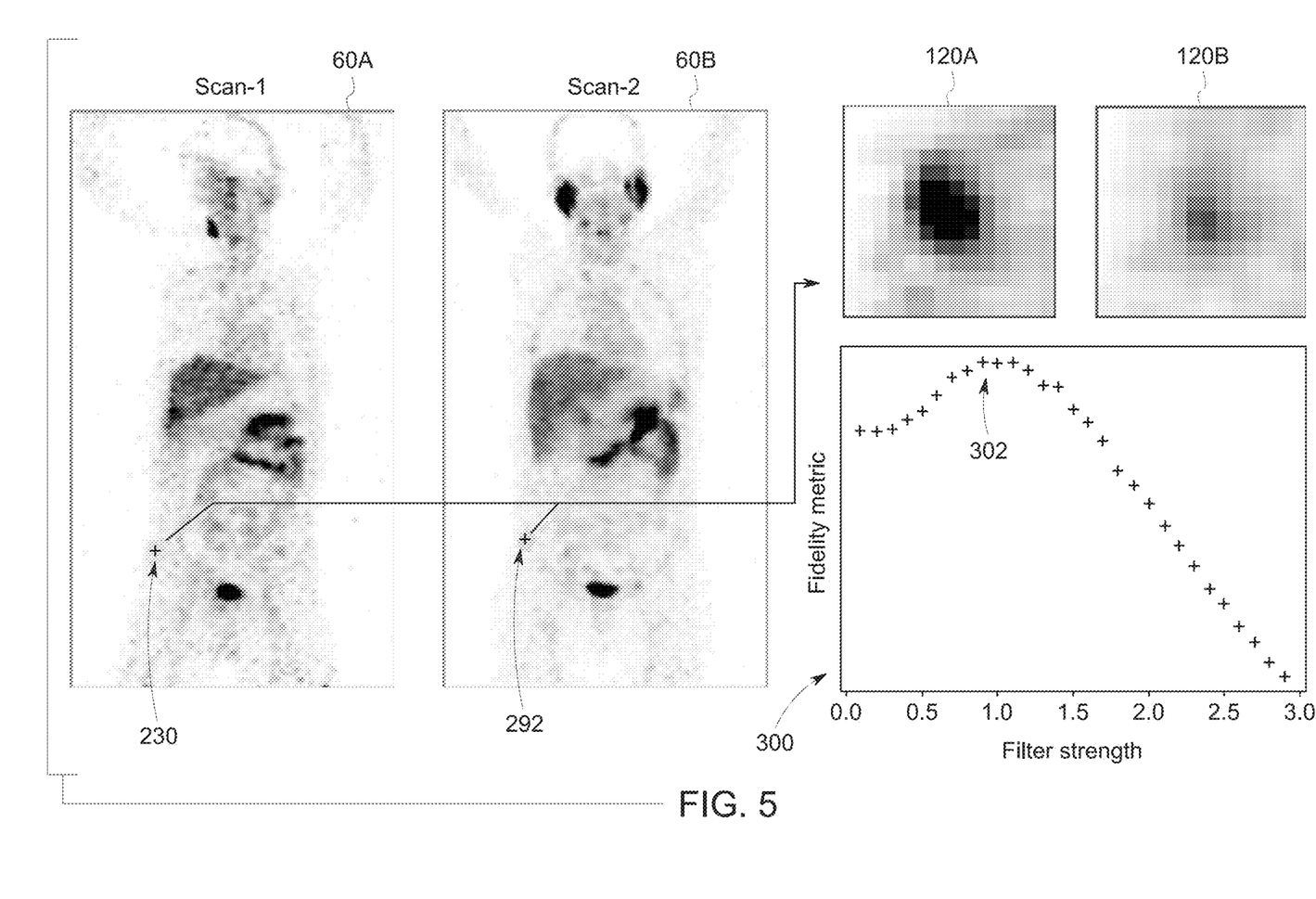
FIG. 5 depicts a visual representation of a pair of scans having corresponding regions of interest for comparison and the selection of a process or process parameters based on maximization of a fidelity metric, in accordance with aspects of the present disclosure.

With the preceding discussion of process steps and flows in mind, an example of these steps with visual references is provided in FIG. 5 to help facilitate understanding. In particular, in this example coronal slices 60A, 60B of two volumetric scans from a Ga-68 PET follow-up study are illustrated and are representative of the two or more image volumes 60 of FIG. 2. A user or an automated routine may select a region of interest (e.g., a candidate lesion at a reference coordinate 230) in one of the two scans, here the first scan 60A. An automated local registration routine identifies the corresponding (i.e., registered) coordinate 292 in the second scan 60B (such that reference coordinate 230 and registered coordinate 292 are corresponding coordinates 68). In this example, the two points are marked on the respective images.

Sub-volumes around the evaluated lesion (sub-volume 120A) and the corresponding sub-volume 120B of the follow-up image volume are automatically determined around the respective reference coordinate 230 and registered coordinate 292. The sub-volume size(s) may be automatically calculated based on the structure sizes. Cross-sections are shown (enlarged) in the depicted example for the two sub-volumes with the primary selected lesion (sub-volume 120A) and the follow-up lesion structure (sub-volume 120B).

As described herein, a fidelity metric 144 is determined or pre-determined. In this example, the fidelity metric 144 is the self-standard deviation of each sub-volume 120 multiplied by the mutual-information function of the two sub-volumes 120. The goal in one such example is to determine optimal Gaussian filter parameters to apply on the input image volumes in order to maximize the fidelity metric 144. With this in mind, the graph 300 shows the calculated fidelity metric 172 as a function of the filter strength. The maximal fidelity 302 is achieved with filter strength around=1.0. The same process can be repeated for additional candidate lesions. The maximum determined for the average curve, across all lesion pairs, corresponds to the overall optimal filter that can be used in processing (e.g., step 190 of FIG. 3) input image volumes 188. As discussed herein, the same technique can be applied with more sophisticated image enhancement methodologies.

While the preceding discussion describes an analytic approach to image improvement and/or standardization which may be useful in the context of follow-up image analysis, a deep learning approach is also contemplated. By way of example, and turning to FIGS. 6 and 7, process flows related to training a deep learning model (FIG. 6) and for the use of such a trained model (FIG. 7) are illustrated. For the purpose of illustration and explanation the present approach is described in terms of general concepts and it should be understood that this approach can be implemented using any suitable network model architecture. To facilitate explanation however, an example is described herein that employs a "Siamese network"-like model architecture in order to provide a concrete example of a possible implementation and to thereby provide a useful and real-world context of such an implementation.

Prior to describing the deep learning network model approach in detail, certain contrasts and distinctions between the presently described technique and other uses of deep learning in image processing may be useful. For example, in contrast to other techniques, and as described in greater detail below, no ground truth images are required in the training of the network model. This is contrary to conventional approaches, which typically employ an inferior image which is processed and the output compared to a ground truth, target image of the same input. In this manner, the network tries to "learn" how to convert the inferior image to be close, as practically possible, to the better ground-truth image. Thus, in conventional designs the network loss function, assumes that there is an exact preferable target to each training input (i.e. the ground truth example). Such approaches have the known limitation that they usually will not learn broader and more general image adaptation goals and concepts. Typically, they instead achieve reasonable generalizability only to new input samples which have image characteristics and features very similar to the used training set. Such conventional approaches may be poorly suited for follow-up imaging and/or functional imaging contexts, in which image characteristics and conditions can span a wide range of options and situations. As a consequence of this limitation, the training set used to train such conventional networks typically includes large amounts of appropriate clinical data.

As discussed in greater detail below, and contrary to such conventional training approaches, the presently disclosed deep learning techniques allow a network model to be trained without use of ground truth training examples. Instead, as described below, training of a network model as disclosed herein is based on comparing the general characteristics of a pair of input image volumes (in each training pass). The paired input image volumes used in training are constructed or selected such that there is a similar underlying structure(s) (among many possible options) but the paired input image volumes also differ in some random feature(s) (such as noise, false-positive-like high-value pixels, fine image artifacts, and so forth). The network design is built such that it learns general image adaptation concepts which can be generalized and applied on a wide range of different input types. Consequently, one advantage to the disclosed techniques relative to prior techniques is that relatively easy to generate synthetic training data set can be used, as opposed to actual clinical sample training data. Specifically, in functional imaging, the trained deep-learning model can "understand", with significant success, the differentiation between probable lesions to noise or to other less significant image features. Therefore, it can assist in the task of lesion follow-up analysis better than conventional approaches.

Figure 6:
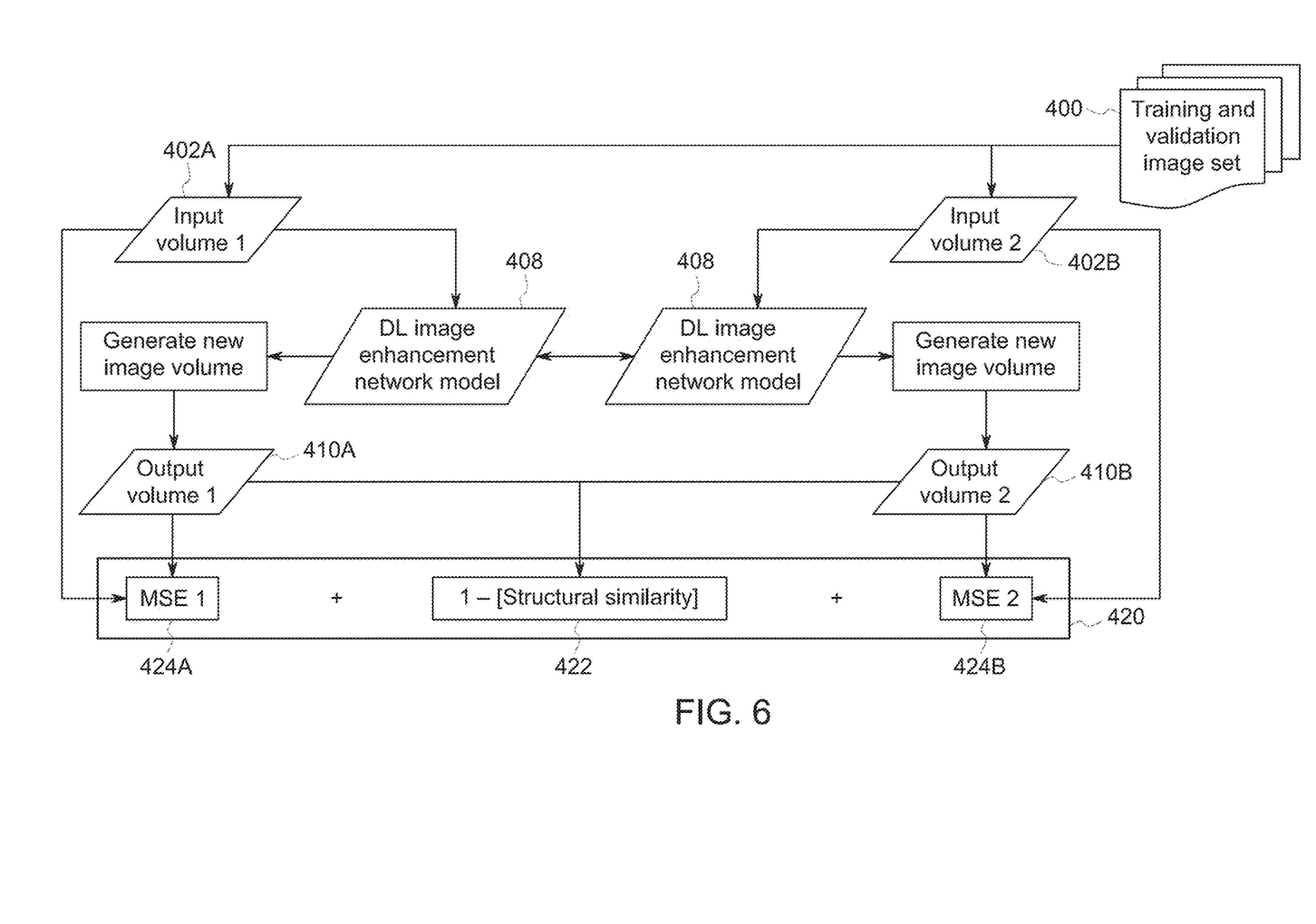
FIG. 6 depicts a process flow of steps employed to train a deep learning network for image volume enhancement, in accordance with aspects of the present disclosure.

With the preceding in mind, as shown in FIG. 6 the deep-learning model training process, in one embodiment, utilizes a training and validation set of image volumes 400. In such an embodiment the training and validation set of image volumes 400 may, entirely or in part, consist of a number (e.g., hundreds, thousands, tens of thousands) of synthetic three-dimensional (3D) structure pairs. Data augmentation such as spatial shifts or rotations can be used as well to increase the variability of the training set.

In one implementation, each structure pair is constructed from a shared specific base shape (e.g., a shared geometric base shape) to which random noise or other random artifacts are applied to generate the two different respective volumes (i.e., the synthetic image volumes differ by the addition of random noise). As a result of this process, each synthetic 3D structure pair includes both similarities (due to the shared base shape used to generate the structure pair) and differences (due to the application of random noise). In such an implementation, dozens (or more) of different base shapes may be employed to generate the synthetic structure pairs. The base shapes may be designed or selected to span some or all (e.g., the majority) of the possible lesion structure space. However, in implementations employing a 'few-shot' network design, it is not necessary that all, or even most of, the possible lesion structures be represented. In practice, on the order of 40-100 different base shapes may be sufficient in such an implementation.

In the depicted example of FIG. 6, a pair of input image volumes 402 containing at least one synthetic 3D structure pair is depicted such that a first input volume 402A includes a first version of a respective synthetic 3D structure and the second input volume 402B includes a second version of the respective synthetic 3D structure where the different versions of the synthetic 3D structure differ based on the random noise (and or other data augmentations) applied to generate each version. Though denoted as input image volumes 402 (and output volumes 410 below) in practice these image volumes may be sub-volumes that are smaller that a full reconstructed diagnostic volume in one or more dimensions. Indeed, for practical and efficiency aspects, it may be noted that the training of the deep learning network model 408 may be done on relatively small sub-volumes (i.e., 25%, 20%, 15%, 10%, 5% or less of a whole or scanned image volume). Further, in practice, the sub-volume size may be determined based on a typical clinical lesion size relevant to the imaging protocol. For example, if lesions in the range of 3 mm-12 mm across are of interest, a sub-volume with side-length of 40 mm may be appropriate, which in relation to a PET image volume may be equivalent to a voxel box of 16ˆ9 voxels. Therefore, the data size of the training set 400 can be reasonably small for practical purpose, and the complication level of the neural network model 408 can be reasonable overall.

In the depicted example scheme the input image volumes 402 are used to train a deep learning network model 408 for image enhancement. Regarding the neural-network structure itself, many possible designs can be appropriate where the input sub-volume 402 and output sub-volume 410 sizes are typically (though not necessarily) equal, such as auto-encoders and decoders, as well as 'U-net' or 'residual U-net' schemes. By way of example, in one embodiment the deep learning network model 408 is an encoder-decoder network type suitable for use with three-dimensional image volumes. In one implementation such a network model may include seven (7) convolution layer blocks that progress in a gradual manner from one (1) to thirty-two (32) channels and, correspondingly, seven (7) deconvolution layer blocks that progress in a gradual manner from thirty-two (32) channels to one channel. Such a network model may include or utilize MaxPool dimensionality reduction.

For the purpose of illustration, the concept of a "Siamese network" is depicted in which two different inputs (here first input volume 402A and second input volume 402B) are input respectively into an identical network 408 (and with the same parameters), and a desired metric (i.e., fidelity metric) is used to compare the two respective outputs (first output volume (or sub-volume) 410A and second output volume (or sub-volume) 410B) to enable the iterative training. In contrast to conventional approaches employing Siamese networks, in which the Siamese networks are used for classification or image differentiation, in accordance with the present techniques the Siamese network is instead used for image enhancement, i.e., to generate a new or enhanced version of an input image.

It may be noted with respect to the described training process flow that in this training flow there is no requirement for a "ground truth" training image to train towards. That is, the proposed deep-learning scheme doesn't require any gold-standard or ground-truth images, nor any clinical data, for the model training. Further, as described herein, the training may be performed with automatically generated synthetic data samples. Correspondingly, and in view of these factors, at least in certain implementations the training method may be characterized as 'un-supervised deep-learning'.

As noted above, and as shown in FIG. 6 the respective input volumes 402A and 402B are processed by identical network models 408 to generate respective output volumes 410A and 410B. After the network model 408 is trained, any input volume or volume pairs that were or were not used for the training may be input to the model 408, and the output volume(s) 410 generated using the network model 408 may be input to a follow-up comparison review by a human reviewer or automated comparison routine. That is, the output volume(s) 410 from the trained network model 408 may be inputs to an image comparison process or other image review or analysis process.

In the training context shown in FIG. 6, the first output volume 410A and the second output volume 410B are used to calculate the pre-determined fidelity metric (e.g., lesion fidelity metric), which serves as a loss function 420, or is used to derive a loss function 420, that is used to train and/or optimize of the deep learning network model 408. In one implementation, the deep learning network model 408 is trained iteratively to maximize the fidelity metric, which in this context corresponds to minimizing the loss function 420.

By way of further example, in one implementation the network model loss function 420 is constructed from both a similarity metric term and additional components that ensure that the new images (i.e., output volumes 410) will not differ too much from the original images (i.e., input volumes 402). In FIG. 6, the loss function 420 incorporates a structural similarity aspect and, as shown in this example, may be implemented as or with the function 422:

$$1-[\text{structural similarity}] \quad (7)$$

so as to facilitate loss function minimization. In this example, the function 422 is a back-propagation differentiable function which enables training convergence. In the depicted example, the two mean square error (MSE) terms 426A and 426B correspond to a degree of difference or deviation between each original sub-volume (i.e., input volumes 402A and 402B) to the corresponding sub-volumes generated by the network model 408 (i.e., output volumes 410A and 401B, respectively). By way of further example, in one implementation for the purpose of weight balancing the term (1-[structural similarity]) is multiplied by an empirical factor (e.g., between 0.01 to 0.1), so as to give nearly equal weights for the different additive components in the loss function. In general, other mutual normalization schemes between the different terms in the loss function can be applied as well.

While the use of sub-volumes having synthetic 3D structure pairs is described primarily above for use in training, use of such synthetic data is not a requirement of training a network model 408 as described herein. In another option, the deep-learning network model 408 can be trained using a set of image volumes that includes, entirely or in part, clinical image sub-volume pairs (i.e., non-synthetic image data). This training image volume set can be constructed, for example, using follow-up pair cases and derived comparable relevant structure pairs. In one option, for each two follow-up clinical cases, an automatic algorithm selects several candidate lesions or other relevant structures with significant probability for having mutual correspondence (at least partially) between the two image sub-volumes. In other options, the training set can be selected with the user assistance using interactive tool and techniques for artificial image data augmentation.

Figure 7:
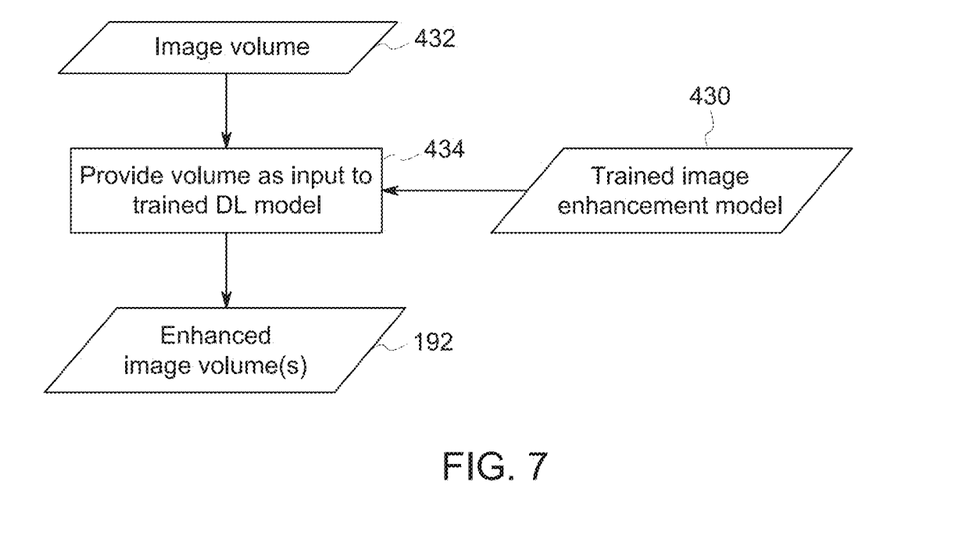
FIG. 7 depicts a process flow of steps employed to enhance image volumes using a trained deep learning network, in accordance with aspects of the present disclosure.

While FIG. 6 illustrates a process flow for training a deep learning image enhancement network model (e.g., neural network) to generate a new, enhanced image volume from an input image volume, FIG. 7 illustrates a process flow for using the trained image enhancement network model 430 (i.e., a trained version of the network model 408 shown in FIG. 6) in a data inference process (i.e., applying the trained model on new image data that was not used for training the network model). In this example an input image volume 432, such as a diagnostic PET or SPECT image volume (or specific lesion sub-volume) acquired as part of a follow-up diagnostic study, is provided as an input (step 434) to the trained image enhancement network model 430. The trained image enhancement network model 430 outputs an enhanced image volume 192 which may be analyzed in place of the input image volume 432 in a reviewer-based or automated follow-up diagnostic analysis. While using deep-learning models as described in the examples above, the dimensions of the input volume 432 (and therefore of the enhanced image 192) can be different than the dimensions of the data used for training (402 in FIG. 6). Therefore, the inference process can be applied on a full clinical imaging volume. By way of example, in one implementation the network model acts on a new input image volume 432 as a function that smooths or reduces noise and artifacts for certain structure types, but enhances (increases values), sharpens, or preserves edges of other structure types. Note that the inference process is applied on each acquired image volume, independently from any other follow-up image volumes, i.e., the processing is not pair-wise or otherwise based on paired follow-up images. Therefore, even image volumes that are not part of a follow-up study can benefit from this enhancement technique.

Figure 8:
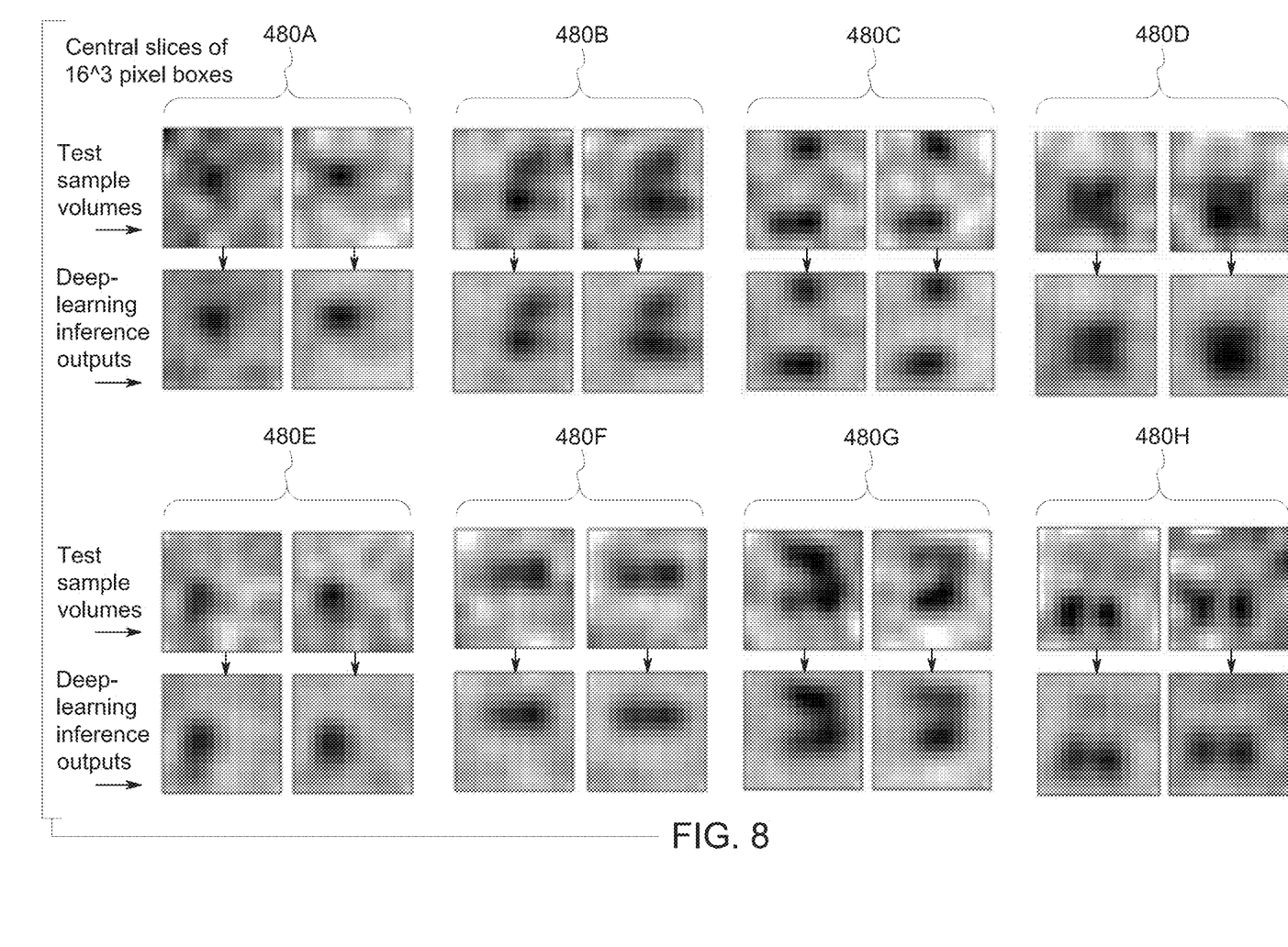
FIG. 8 depicts arbitrary sub-volume pairs processed using a deep learning network model, in accordance with aspects of the present disclosure.
Figure 9:
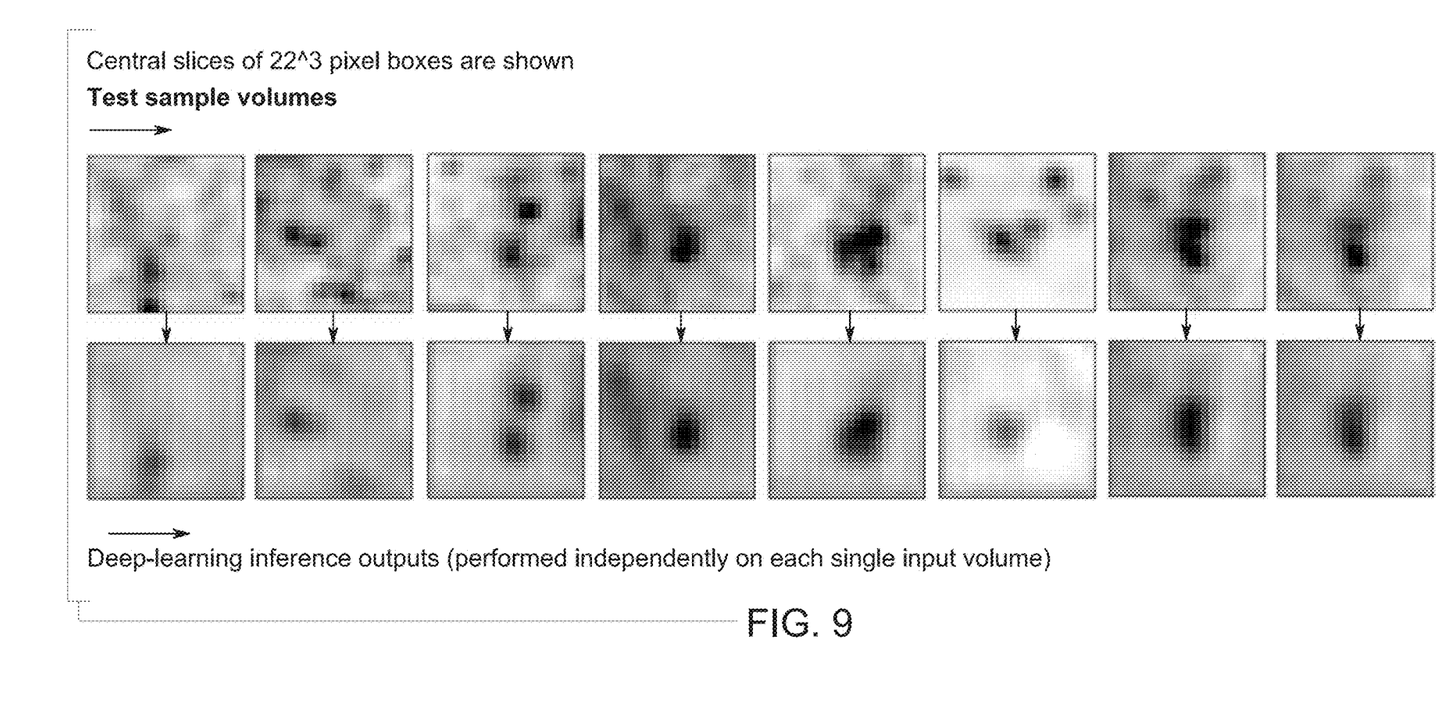
FIG. 9 depicts lesion-like samples in noisy environment processed using a deep learning network model, in accordance with aspects of the present disclosure.

With the preceding in mind, FIGS. 8 and 9 depict example input and output image volumes used and/or generated in accordance with the deep learning network model discussed herein. Turning to FIG. 8, an example of eight arbitrary sub-volume pairs 480A-480H from a network model validation set are shown. For the purpose of illustration, a central slice of $16^3$ pixel boxes is depicted for each respective sub-volume. For each sub-volume pair 480, the respective input sub-volumes are shown in the top row and the corresponding output sub-volumes of the trained deep learning network model 430 are depicted beneath the respective inputs. As can be seen, after the inference the main features of the base structures are preserved while the noise is significantly reduced. Moreover, the similarity between the two image volumes of a pair 480 is increased.

Turning to FIG. 9, an example of eight lesion-like samples in a noisy environment is illustrated. The sample images were taken from four clinical $^{68}$Ga-PET cases and the images are illustrated before (top row) and after (bottom row) processing using a trained deep learning network model (i.e., inferencing). As in the preceding example, to facilitate illustration in two-dimensions, a central slice of $22^3$ pixel boxes is depicted for each respective sub-volume. As noted herein, each sub-volume is passed independently through the trained network model 430. In this example, the deep-learning network model 430 was trained only on synthetic structure data set as described herein (i.e. not on clinical image volume data).

Technical effects of the invention include training and use of a network model for image enhancement. In certain implementations, the network model is trained without use of ground truth training examples. In such an example, training of the network model may be based on comparing the general characteristics of a pair of input image volumes in each training pass. The paired input image volumes used in training may be synthetic and may be constructed such that there is a similar underlying structure(s) but also differ in some random feature(s) (such as noise, false-positive-like high-value pixels, fine image artifacts, and so forth). Alternatively, the image enhancement maybe based on optimization or parameterization of an analytic process or processes that is trained to optimize or satisfy a fidelity metric criterion. The parameterized process(es) may subsequently be used to process diagnostic images. In both the deep learning and analytic approaches, the trained model or process may be used to process individual images (i.e., non-paired images), including images acquired as part of a follow-up study, to generate an output image better suited for analysis or comparison.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An image processing system, the image processing system comprising:
   one or more memory structures storing processor-executable code; and
   one or more processors in communication with the one or more memory structures, wherein the processor-executable code, when executed by the one or more processors, cause the one or more processors to perform acts comprising:
   training a deep learning network model for image enhancement by iteratively performing steps comprising:
      receiving a first input image volume and a second input image volume, wherein the first input image volume comprises a first version of a synthetic three-dimensional (3D) structure and the second input image volume together comprises a second version of the synthetic 3D structure, wherein the first version of the synthetic 3D structure and the second version of the synthetic 3D structure comprise a shared base shape but differ based on different random noise or other random artifacts being applied to each of the first version and second version;
      providing the first input image volume and the second input image volume to the deep learning network model, wherein the deep learning network model is configured to respectively output a first output image volume and a second output image volume;
      comparing the first output image volume and the second output image volume based on a fidelity metric comprising a measure of structural similarity, wherein a loss function for the deep learning network model is based on the fidelity metric and training the deep learning network model is based on reduction or minimization of the loss function.

2. The image processing system of claim 1, wherein the processor-executable code, when executed by the one or more processors, cause the one or more processors to perform further acts comprising:
   providing an input image volume to the deep learning network model to generate an enhanced image volume; and
   providing the enhanced image volume for review as part of a follow-up analysis.

3. The image processing system of claim 1, wherein the deep learning network model is configured as a Siamese network.

4. The image processing system of claim 1, wherein training the deep learning network model does not utilize ground-truth training images.

* * * * *